United States Patent
Abele

[11] Patent Number: 5,860,974
[45] Date of Patent: Jan. 19, 1999

[54] HEART ABLATION CATHETER WITH EXPANDABLE ELECTRODE AND METHOD OF COUPLING ENERGY TO AN ELECTRODE ON A CATHETER SHAFT

[75] Inventor: John E. Abele, Concord, Mass.

[73] Assignee: Boston Scientific Corporation, Natick, Mass.

[21] Appl. No.: 797,720

[22] Filed: Feb. 11, 1997

Related U.S. Application Data

[63] Continuation of Ser. No. 654,751, May 29, 1996, abandoned, which is a continuation of Ser. No. 86,543, Jul. 1, 1993, abandoned.

[51] Int. Cl.$^6$ .......................... A61B 17/39; A61B 5/042; A61N 1/05
[52] U.S. Cl. .......................... 606/41; 600/374; 600/439; 600/467; 600/470; 607/99; 607/122
[58] Field of Search .................. 606/41; 607/98, 607/99, 122, 126; 600/374, 381, 439, 467, 470

[56] References Cited

U.S. PATENT DOCUMENTS

| | | | |
|---|---|---|---|
| 2,032,859 | 3/1936 | Wappler | 174/89 |
| 2,043,083 | 6/1936 | Wappler | 128/303.11 |
| 2,126,070 | 8/1938 | Wappler | 128/172.1 |
| 4,407,294 | 10/1983 | Vilkomerson | 128/660 |
| 4,641,649 | 2/1987 | Walinsky et al. | 128/303.1 |
| 4,676,258 | 6/1987 | Inokuchi et al. | 128/804 |
| 4,709,698 | 12/1987 | Johnston et al. | |
| 4,776,349 | 10/1988 | Nashef | 607/122 |
| 4,821,731 | 4/1989 | Martinelli et al. | 128/662.06 |
| 4,841,977 | 6/1989 | Griffith et al. | 128/660.03 |
| 4,936,301 | 6/1990 | Rexroth et al. | 606/45 |
| 4,940,064 | 7/1990 | Desai | 607/122 |
| 4,951,677 | 8/1990 | Crowley et al. | 128/662.06 |
| 4,955,377 | 9/1990 | Lennox et al. | |
| 5,000,185 | 3/1991 | Yock | 128/662.03 |
| 5,054,492 | 10/1991 | Scribner et al. | 128/662.06 |
| 5,103,804 | 4/1992 | Abele et al. | |
| 5,106,360 | 4/1992 | Ishiwara et al. | 600/2 |
| 5,131,397 | 7/1992 | Crowley | 128/662.06 |
| 5,140,987 | 8/1992 | Schuger et al. | 128/642 |
| 5,156,151 | 10/1992 | Imran | |
| 5,170,805 | 12/1992 | Kensey et al. | 128/898 |
| 5,222,501 | 6/1993 | Ideker et al. | 128/660.03 |
| 5,255,678 | 10/1993 | Deslauriers et al. | 607/122 |
| 5,263,493 | 11/1993 | Avitall | 128/642 |
| 5,277,201 | 1/1994 | Stern | 607/99 |
| 5,313,943 | 5/1994 | Houser et al. | 606/41 |

(List continued on next page.)

FOREIGN PATENT DOCUMENTS

| | | | |
|---|---|---|---|
| 3516830 | 11/1986 | Germany | 607/99 |
| 1220673 | 3/1986 | U.S.S.R. | 607/126 |
| 1690786-A1 | 11/1991 | U.S.S.R. | |
| WO 92/03095 | 3/1992 | WIPO | |

OTHER PUBLICATIONS

Berns et al., "Feasibility of Radiofrequency–Powered, Thermal Balloon Ablation of Atrioventricular Bypass Tracts Via the Coronary Sinus"; Nov. 11–14, 1991, Anaheim Convention Center, Anaheim CA.

(List continued on next page.)

*Primary Examiner*—Lee S. Cohen
*Attorney, Agent, or Firm*—Lyon & Lyon LLP

[57] ABSTRACT

An expandable ablation electrode is provided on a catheter constructed to access the heart. When the electrode is introduced to the heart, it is small and suitably flexible to maneuver through the torturous path. However, when the catheter is in place in the heart, the electrode is expansible in diameter to a substantially larger dimension, and is relatively rigid, enabling a large conductive surface to press against the heart tissue with the desired contact pressure. When RF energy is then applied to the electrode it produces a burn lesion of desired large size and depth. This overcomes the limitations to size that have been encountered using conventional rigid electrodes.

22 Claims, 6 Drawing Sheets

U.S. PATENT DOCUMENTS

| | | | |
|---|---|---|---|
| 5,325,860 | 7/1994 | Seward et al. | 128/662.06 |
| 5,334,193 | 8/1994 | Nardella | 606/41 |
| 5,344,398 | 9/1994 | Hara | 604/96 |
| 5,345,936 | 9/1994 | Pomeranz et al. | 128/642 |
| 5,348,554 | 9/1994 | Imran et al. | 606/41 |
| 5,403,311 | 4/1995 | Abele et al. | 606/49 |
| 5,540,679 | 7/1996 | Fram et al. | 606/27 |

OTHER PUBLICATIONS

Calkins et al., "Diagnosis and Cure of the Wolff–Parkinson–White Syncrome or Paroxysmal Supraventricular Tachycardias During A Single Electrophysiologic Test"; *N.E. Journal of Med.*, vol. 324, No. 23, Jun. 6, 1991.

Crowley et al., "Optimized Ultrasound Imaging Catheters for Use in the Vascular System"; *International Journal of Cardiac Imaging* 4:145–151, 1989.

Crowley et al., "Ultrasound Guided Therapeutic Catheters: Recent Developments and Clinical Results"; *International Journal of Cardiac Imaging*, 6:145–156, 1991.

Ellis et al., "Ultrasonic Imaging Catheter"; Microvasive, Inc.; 1988.

Jackman et al., "Catheter Ablation of Accessory Atrioventricular Pathways (Wolff–Parkinson–White Syndrome) by Radiofrequency Current"; *N.E. Journal of Med.*, vol. 324, No. 23, Jun. 6, 1991.

Lesh, "Application of Ultrasound Imaging to Catheter Ablation of Cardioac Arrhythmias"; *Biomedical Business International;* (date unknown).

McMath, "Percutaneous Laser Balloon Coagulation of Accessory Pathways"; *SPIE,* vol. 1425, pp. 165–169; 1991, Schuger et al., "Long–Term Effects of Percutaneous Laser Ballon Ablation from the Canine Coronary Sinus"; pp. 947–954; May 18, 1992.

Schuger al., "Percutaneous Transcatheter Laser Ballon Ablation from the Canine Coronary Sinus: Implications for the Wolff–Parkinson–White Syndrome", *Lasers In Surgery and Medicine,* vol. 10, No. 2, 1990.

Polaris Series Steerable/Deflectable Tip Mapping Catheters brochure, Mansfield Boston Scientific Corporation.

Explorer Series Electrophysiology Mapping Catheters brochure, Mansfield Boston Scientific Corporation.

Explorer 360° Series Advanced Electrophysiology Mapping Catheters brochure, Mansfield Boston Scientific Corporation.

Gold Probe—The Next Generation in Bipolar Hemotasis brochure, Microvasive Boston Scientific Corporation.

Advanced Materials & Processes Surface Engineering, ASM International, Dec. 1990 vol. 138 Issue 6.

Anatomy and Physiology brochure, Mansfield Boston Scientific.

Frank et al., Implantable cardioverter–defibrillators: alternative treatment for ventricular tachyarrhythmias, Mar. 1992, vol. 3, No. 3, Coronary Artery Disease, 1992 Current Science ISSN 0954–6928.

Becker et al., Radiofrequency Baloon Angioplasty Rationale and Proof of Principle, Nov. 1988, Investigative Radiology, vol. 23, pp. 810–817.

Critelli, Transcatheter Aglation of Tachyarrythmias: An Evolving Therapeutic Procedure, 1989, Journal of Interventional Cardiology, vol. 2, No. 4, pp. 233–236.

Buxton, Catheter Ablation of Atrioventricalar Bypass Tracts Still an Investigational Procedure, Jun. 1989 Circulation, vol. 79, No. 6, pp. 1388–1390.

Borggrefe et al., Electrophysiology, Pacing, and Arrhythmia, Catheter Ablation Using Radiofrequency Energy. Feb. 1990, Clin. Cardio. 13, 127–131.

Avitall et al., The Physics and Engineering of Transcatheter Cardiac Tissue Ablation, University of Wisconsin–Milwaukee Clinical Campus.

Interventional Electrophysiology Poised for Growth, Sep. 12, 1991, The BBI Newsletter, vol. 14, No. 9 pp. 162–165.

McGuire et al., Surgical techniquest for the cure of atrioventricular junctional reentrant tachycardia, Mar. 1992, Coronary Artery Disease, vol. 3, No. 3. pp. 186–191.

Selle, Definitive surgery for postinfarction ventricular tachycardia, Mar. 1992, Coronary Artery Disease, vol. 3, No. 3. pp. 204–209.

Mahomed et al., Surgery for Wolff–Parkinson–White syndrome, 1992 Current Science ISSN 0954–6928, pp. 175–185.

Sung, Arrhythmias and the Autonomic Nervous System, Sep. 1987, Cardio, pp. 77–80.

The Soft Steerable Catheter System for Rapid GI Intubation and Decompression and Sampling, Oct. 1978 Medi Tech Division Cooper Scientific Corporation.

Becker et al., Original Investigations: Radiofrequency Baloon Angioplasty Rationale and Proof of Principle, Nov. 1988 Investigative Radiology, vol. 23, pp. 810–817.

Tarjan et al., An experimental Device for Low–Energy, Precise Ablation of AV Conduction, Nov.–Dec. 1986, PACE vol. 9, pp. 1396–1402.

Saksena et al., Low–energy transvenous ablation of the canine atriobentricular conduction system with a suction electrode catheter, Aug. 1987, Circulation, vol. 76, No. 2, pp. 394–403.

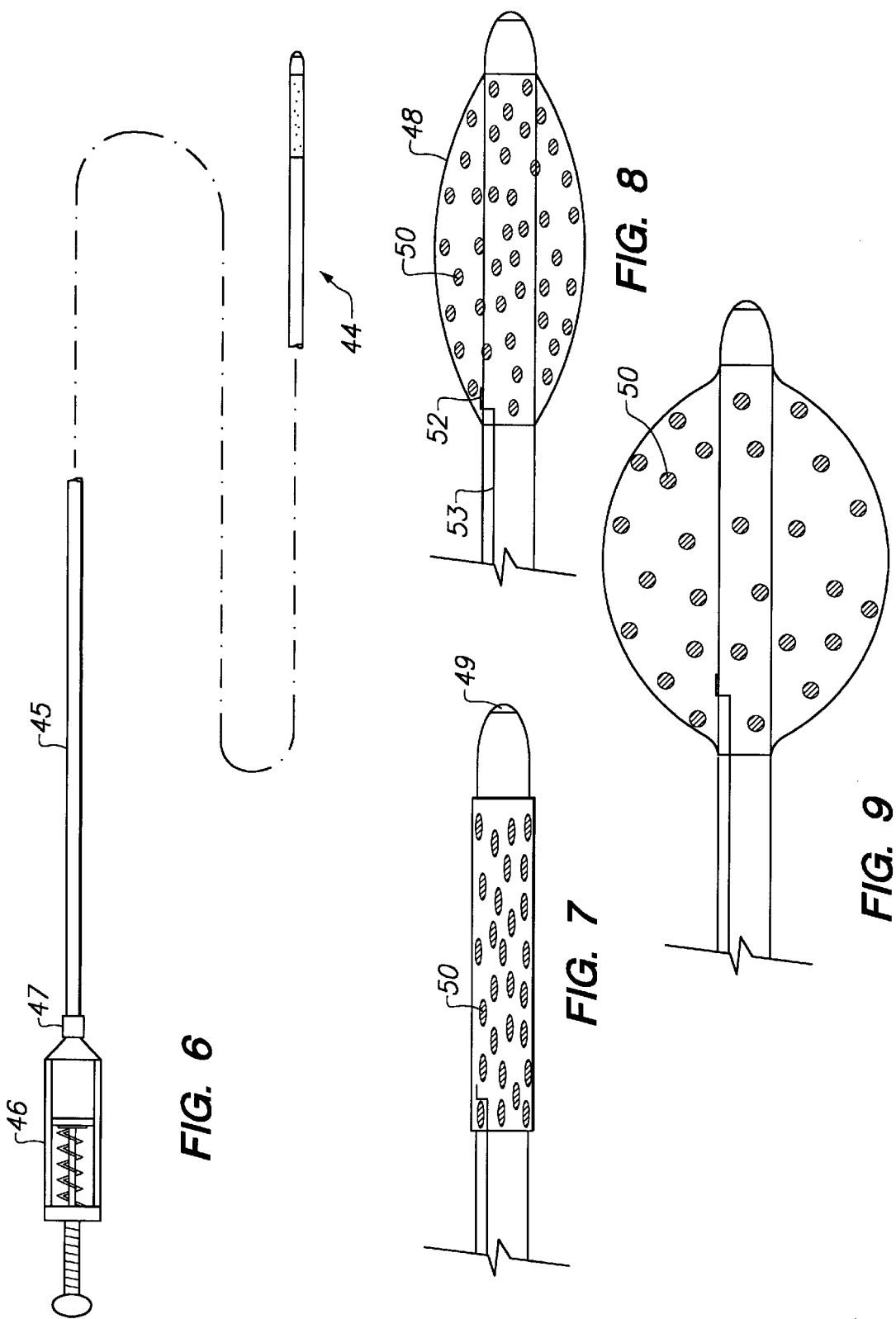

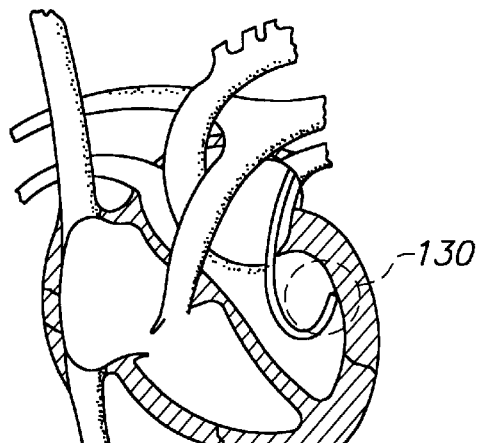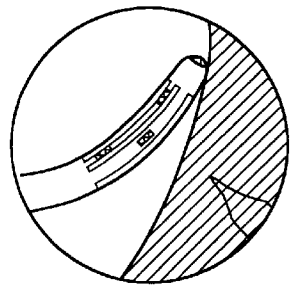
FIG. 22  FIG. 23
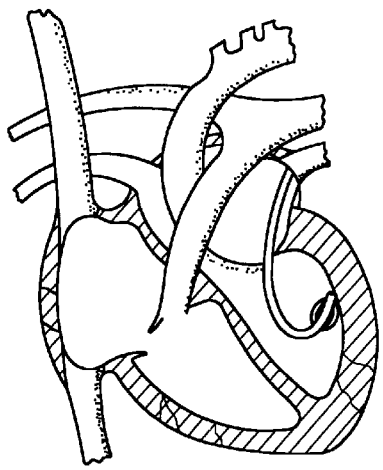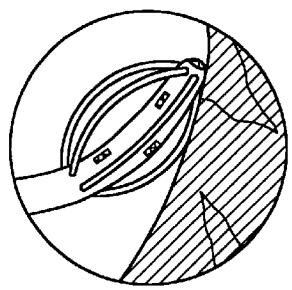
FIG. 24  FIG. 25
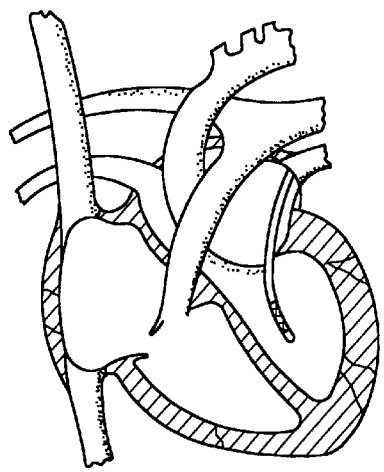
FIG. 26

HEART ABLATION CATHETER WITH EXPANDABLE ELECTRODE AND METHOD OF COUPLING ENERGY TO AN ELECTRODE ON A CATHETER SHAFT

This application is a continuation of application Ser. No. 08/654,751, filed May 29 1996, now abandoned, which is a continuation of application Ser. No. 08/086,543 filed Jul. 1, 1993, now abandoned.

BACKGROUND OF THE INVENTION

The present invention relates to heart ablation catheters.

Electrophysiological catheters apply radio frequency energy to produce burn lesions at selected points in the heart to correct arrhythmias. By destroying the cells that constitute defective conductive pathways, the arrhythmias are stopped. Typically, rigid electrodes, of ring form either partially or totally surrounding the catheter shaft, are used, though it is desirable at times to produce larger lesions than can be produced with such electrodes. By using a larger electrode, one could apply higher power, and by spreading the current at conventional current intensity over a larger area, the larger lesion can be produced. The diameter of such conventional electrodes, however, has been limited by the size of access hole that can be tolerated in the artery. Also, the length of these electrodes has been limited by the need to maintain maneuverability for the catheter to pass through tight curves in proceeding through the arterial system and into the heart.

SUMMARY OF THE INVENTION

The present invention provides a catheter with an expandable ablation electrode constructed to access the heart. When it is introduced to the heart, the electrode is small and suitably flexible to maneuver through the torturous path. However, when the catheter is in place in the heart, the electrode is expansible in diameter to a substantially larger dimension, and is relatively rigid, enabling a large conductive surface to press against the heart tissue with the desired contact pressure. When RF energy is then applied to the electrode it produces a burn lesion of desired large size and depth. This overcomes the limitations to size that have been encountered using conventional rigid electrodes.

According to one preferred embodiment, there is provided on the electrophysiology catheter, a balloon the exterior of which is coated uniformly with a conductive material, preferably gold, or other material that is both electrically and thermally conductive. Such conductive coating materials can be deposited on the surface of the material forming the balloon, by conventional vacuum deposition techniques, or a thicker coating of gold for larger current capacity can be produced with electroplating techniques.

Substantial thermal conductivity of the electrode material is important to prevent heat build-up in the electrode which might cause sticking of the electrode to tissue, or if the temperature gets high enough, even cause the thin electrode layer to deteriorate.

In preferred embodiments, a balloon of the type commonly used for balloon angioplasty dilatation, is employed. Such a balloon is made of a very strong, low elongation resinous material such as PET (polyethylene terepthalate). As is known, PET can be formed into a balloon of thin wall thickness using modified bottle blowing techniques. Such a balloon, in uninflated state, is folded about the catheter using folding techniques commonly applied to dilatation balloons to achieve the size corresponding substantially to that of the catheter on which it is mounted.

The dimension of the balloon is enlarged during use by infusing into the balloon fluid containing a significant concentration of radiopaque contrast agent such as the conventional viscous inflation fluid used for balloon dilatation.

Inflation causes the balloon to unfold and to expand to its set, relatively large diameter. By inflating to high pressure, e.g. 5 or more atmospheres, the enlarged balloon becomes significantly rigid.

Typically, the balloon is of a set length, which may be substantially longer than conventional rigid electrodes. When in deflated condition, at its smaller dimension, it and the portion of the catheter on which it is carried is sufficiently flexible to enable maneuvering through the tight bends of the arterial system and into the heart. Upon inflation, the rigidity of the expanded, pressurized balloon is realized to be appropriate for effective RF ablation.

A degree of rigidity is an important requirement because the electrode must push against the heart tissue with pressure to cause the heart tissue to conform to the electrode shape and establish good, uniform electrical contact. The degree of conformity and the uniformity of pressure along the length of the balloon is facilitated in the present invention by operation of Pascal's law, which enables pressure against the tissue to be equilibrated.

In the case of balloons comprised of PET, a power supply conductor is attached to the conductive coating at the proximal or rearward end of the balloon, on the exterior surface. The conductor such as a wire, is lead through the wall of the catheter and through the shaft to appropriate terminal at the proximal end.

In another embodiment, the balloon is made of more compliant material than PET. In one case, advantageous for certain purposes, the balloon is comprised of an elastomer. Due to its elasticity, one cannot only change the diameter from small to large, but one can chose the particular inflated dimension over a range by careful metering of the inflation fluid into the balloon. Thus there is achievable an electrode having an inflated dimension that may be selected from between e.g. 5 mm and 10 mm, depending on the size of the lesion the physician desires to create. This provides to the user the option, after introduction of the catheter of, establishing a first electrode shape, and size of the lesion to be produced, by introducing a preselected volume of fluid. Typically the operating physician may choose to produce the smallest region possible that in his judgment may cure the arrhythmia. Therefore he may initially start with the balloon inflated to 5 mm, and only increase its size if deeper and larger lesions are found to be necessary. The balloon size can be increased by metered addition of additional inflation fluid.

For the purpose of controlling the size of the inflation of the expansible balloon, a high accuracy screw syringe is employed to precisely control the amount of fluid introduced to the balloon. The type of screw syringe used for balloon angioplasty is suitable for this purpose.

The balloon can be seen on the fluoroscope due to the contrast agent in the inflation fluid, and its size can be fluoroscopically judged. Thus one can control the diameter with the amount of fluid introduced and one can monitor its size fluoroscopically.

In the case of the elastomeric, variable sized balloon, in order to allow the balloon to expand and contract, the electrode coating on the outside of the balloon, is of a pattern chosen to enable the balloon to stretch. In one case it may be a serpentine pattern of narrow conductive elastomeric stripes on the balloon surface that effectively hinge while maintaining continuity as the balloon expands, to accommodate the change in geometry. In another embodiment a series of metal conductive dots is applied to the exterior of the balloon, while flexible, narrow conductive paths may be defined to introduce power to the dot-shaped electrodes.

Another technique for introducing energy to the dots may be by capacitive coupling. In this case, electrically conductive fluid is employed as the inflation medium for the balloon. Monopolar RF energy is applied to the fluid via an electrode fixed to the exterior of the portion of the catheter shaft that extends through the balloon, and capacitive coupling occurs across the thickness of the balloon to the conductive coated dots on the outside of the balloon.

Instruments described so far are intended for monopolar operation. There is typically only one electrode on the catheter and the current is conducted through the tissue to another electrode in the form of a ground plate that has a surface area many times that of the catheter electrode. This ground plate is maintained in contact with the skin of the patient. Because of the large size of the ground plate, when the current reaches it, the density is so low that no burning or heating occurs, as is well known.

In certain instances, however, the balloon is advantageously constructed for bipolar introduction of RF current to the tissue. This can be advantageous for cases where one wishes to create a large area lesion but not cause deep penetration. This may be useful in the case of diseased arrhythmia producing tissue that lies only near the surface.

In one preferred embodiment, a balloon has two annular bands of conductive material on its exterior for bipolar operation, with the RF current flowing through the tissue between the two bands.

Other ways to construct the balloon will occur to those skilled in the art. For instance, a balloon may be of electrically conductive material such as conductive elastomer filled with silver particles.

Other examples of operable, expansible electrodes include mechanical structures.

The first preferred mechanical device is comprised of a series of expansible members that are constrained either by spring force or mechanical force so that when they are uncovered, in the manner of a conventional stone retrieval basket sold by Boston Scientific Corporation, the wire ribbons expand outward and provide a larger electrode surface for engagement of the tissue with suitable pressure.

In one instance a straight cage formed of spring wires that are generally axially disposed is employed. It is so constructed that when the wires are released by removal of the sheath, they are allowed to expand to a rest dimension of generally spherical shape. Self-expanding wires may be constructed of conductive spring metal or a relatively poor conductor with good spring properties can be employed such as nitinol on which is deposited a highly conductive material such as gold. For such a self-expanding embodiment, as mentioned, a constraining sheath is employed. It confines the springy wires in distorted condition at a much smaller diameter. Upon removal of the sheath, such as sliding it proximally of the catheter, the spring wires are released to form the rounded shape.

In another embodiment, a tension wire can be employed which acts to pull the wires of the basket structure radially inwardly to keep the wires close to the shaft during introduction. Release of tension on the tensioning wire enables the structure to expand radially to its enlarged rest condition.

In another embodiment, a central member independent of the outer catheter wall is employed to move the distal tip of the spring basket distally independently of the proximal end, to reduce the diameter of the basket by pulling it axially. Release allows the distal tip to draw back and the electrode basket to expand.

Other variations of this aspect are a spiral cage and a braided weave each made of heat conductive, electrically conductive wires. These again are embodiments in which the wire members lie close to the shaft in the reduced sized state and expand to the larger diameter in the released or expanded state. Such more complex structures are preferable in cases where it is desired to maximize the wire contact coverage when the basket is expanded.

In many instances use of the balloon is preferred to obtain the most uniform distribution of energy, but there are instances in which the mechanical structures have advantage, such as for conforming to special profiles of particular locations of the heart cavity.

In certain embodiments, a further electrode is disposed on the portion of the shaft that protrudes beyond the balloon. Such an electrode can be used for producing small area ablation, when desired, to increase the capability of the single catheter. The distal electrode may also be employed, along with additional electrodes, for instance, ring electrodes on the catheter shaft both proximal and distal of the balloon, for electrophysiological mapping. In some cases, it is preferred to activate the mapping electrodes simultaneously while performing ablation. In this way, the change in the electrical activity of the adjacent tissue can be monitored as ablation proceeds, thus to produce an indication monitoring of the result being produced. Control of the duration of the application of the RF current may be determined by the detected values.

It is also advantageous in certain instances to employ ultrasound imaging in connection with the ablation technique to observe the lesion forming and to measure its dimension.

In certain instances, it is advantageous to provide a fluid dispensing lumen as part of the catheter for the purpose of augmenting the ablation effect at the tissue. The fluid may be selected to be highly electrically conductive relative to the conductivity of blood and thus can render the zone where the fluid is introduced preferentially conductive, to establish a zone that tends to concentrate the heat, as a result of $I^2R$ losses being greatest where the largest current flows.

In another instance, fluid introduced through the lumen is selected to be destructive of tissue, such as alcohol which tends to be ablative due to its osmotic behavior. In this way fluid ablation and RF ablation effects can be advantageously combined.

In preferred embodiments, the catheter is of 7 French size. The balloon in deflated condition in this case is also about 7 French and is expansible to e.g. 5 or 10 mm in diameter.

A principal advantage of the invention is that it enables larger lesions to be created with a single catheter to achieve a definitive result for the patient in less time, hence with less risk to the patient and better utilization of the physician's time, than with prior electrodes.

Thus advantages of the present invention are that quite large electrodes can be achieved which act faster and can produce lesions deeper than prior devices, all in a device that is practical to maneuver through the arterial system and into the heart. The instrument is useful in any chamber of the heart where it is desired to produce a large lesion.

Numerous other features, objects and advantages of the invention will become apparent from the following detailed description when read in combination with the accompanying drawings.

BRIEF DESCRIPTION OF THE DRAWINGS

FIG. 6 is a schematic view of an electrophysiological heart catheter coupled to an inflation metering device.

FIG. 7 is a side view of a distal portion of the electrophysiological heart catheter of FIG. 6, showing a deflated balloon having a plurality of conductive dots mounted on its surface.

FIG. 8 is a side view of the distal portion of the electrophysiological heart catheter of FIG. 6, showing the balloon partially inflated.

FIG. 9 is a side view of the distal portion of the electrophysiological heart catheter of FIG. 6, showing the balloon more fully inflated.

FIG. 22 is a partially cross-sectional view of a catheter in the left side of a heart, showing a mechanical electrode in a non-expanded condition and in contact with heart tissue.

FIG. 23 is an enlarged view of a portion of FIG. 22.

FIG. 24 is a partially cross-sectional view of a catheter in the left side of a heart, showing a mechanical electrode in an expanded condition.

FIG. 25 is an enlarged view of a portion of FIG. 24.

FIG. 26 is a partially cross-sectional view of a catheter in the left side of the heart, showing a mechanical electrode in a non-expanded condition and removed from contact with heart tissue.

DETAILED DESCRIPTION

Figure 1:
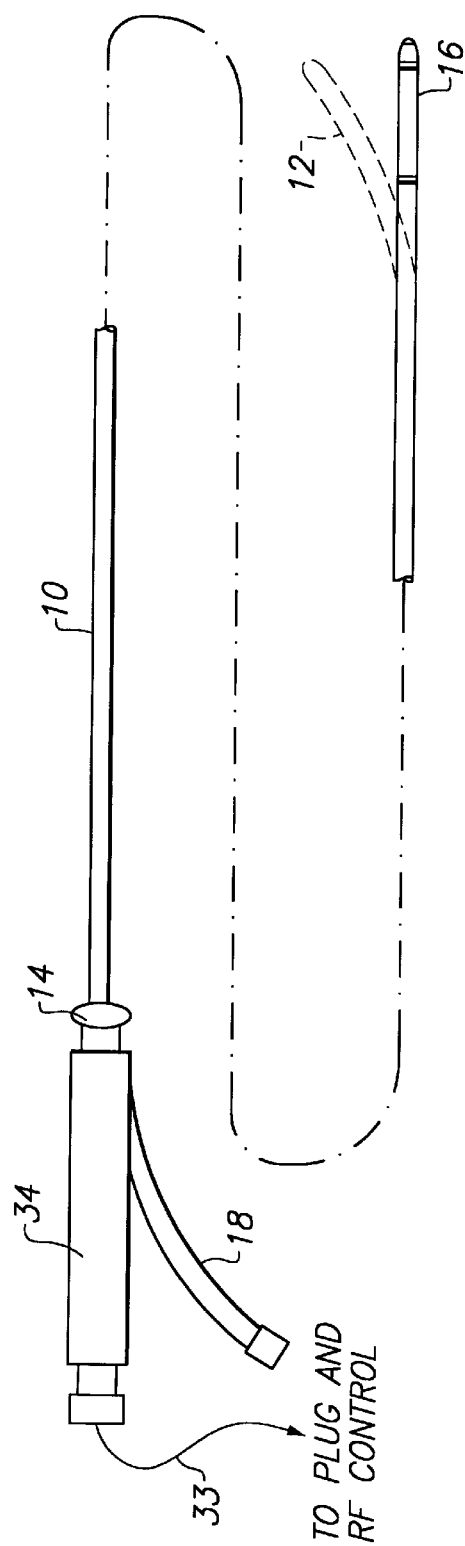
FIG. 1 is a schematic view of an electrophysiological heart catheter.

FIG. 1 shows, in schematic view, an electrophysiological heart catheter comprising catheter shaft 10 including deflectable tip 12 and deflection actuator 14. On the deflectable portion 12 an expansible balloon 16 is included. At the proximal end an introductory lumen 18 communicates with a source of inflation fluid under pressure. An inflation lumen extending through the catheter shaft connects the interior of the balloon with the introductory lumen 18 for inflation of the catheter.

Figure 2:
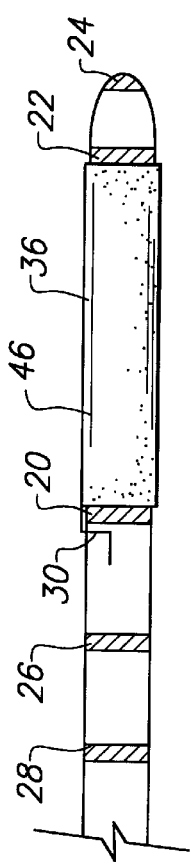
FIG. 2 is a side view of a distal portion of the electrophysiological heart catheter of FIG. 1, having a deflated balloon.

Referring to FIG. 2, the catheter has ring electrodes 20 and 22 at the respectively proximal and distal ends of the balloon 16. A tip electrode 24 and further ring electrodes proximal of the balloon 26 and 28 are also included. An electrical power source wire 30 makes electrical contact with a conductive coating 32 that is generally applied over the balloon surface. As suggested, the wire proximal of the balloon passes inwardly through the wall thickness of the catheter and then proceeds to the proximal end where it connects to a cable 33 that couples to a suitable RF control unit. The handle 34 is grasped while moving the actuator 14 axially to cause deflection as suggested in the dotted lines in FIG. 1.

As seen in FIG. 2, the balloon in uninflated condition has a diameter substantially corresponding to that of the catheter. Fold lines 36 are shown suggesting that the balloon is folded in the way employed with dilatation catheters.

Figure 3:
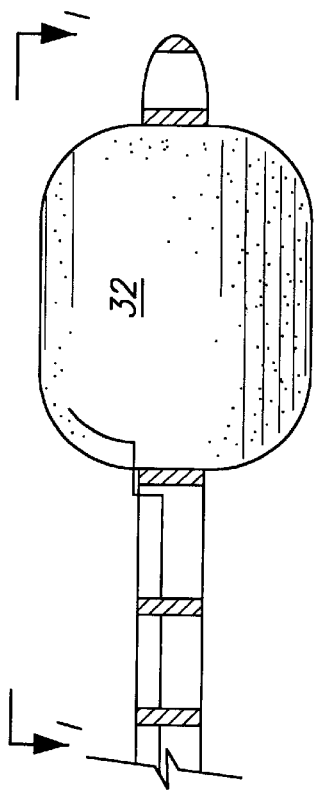
FIG. 3 is a side view of a distal portion of the electrophysiological heart catheter of FIG. 1, having an inflated balloon.

In FIG. 3 the balloon is shown to be inflated, e.g. at 8 to 10 atmospheres. So inflated the balloon becomes quite rigid and capable of pressing against heart tissue sufficiently to make good electrical contact. The area of tissue contacted is in proportion to the diameter of the balloon which as can be seen in FIG. 3, when inflated can be as much as three times as large as the diameter of the shaft per se.

Figure 4:
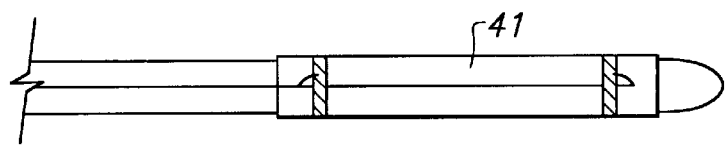
FIG. 4 is a side view of a distal portion of an electrophysiological heart catheter having a deflated balloon with two conductive stripes applied to the surface of the balloon.
Figure 5:
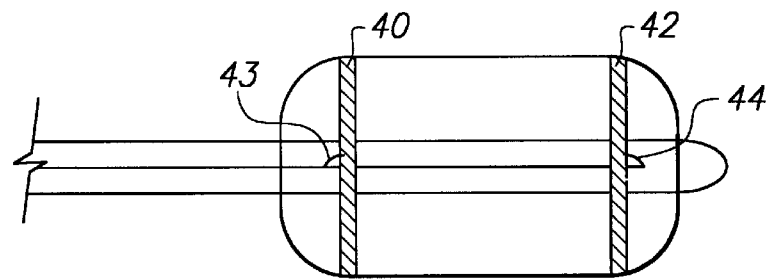
FIG. 5 is a side view of the electrophysiological heart catheter of FIG. 4, with the balloon in its inflated state.

The embodiment of FIGS. 4 and 5 employs a similar catheter shaft and a similar balloon material. In this case, two axially spaced-apart conductive stripes 40 and 42 are applied to the balloon surface, preferably made from gold. In this embodiment, RF current is introduced in a bipolar manner for ablating surface tissue.

FIG. 4 indicates that the balloon 41 can fold in a similar manner as the balloon of FIG. 2 to conform substantially to the size of the catheter.

FIG. 5 shows the balloon inflated, e.g., at 8 to 10 atmospheres. Electrical leads 43 and 44 deliver the RF current to the conductive stripes.

FIG. 6 shows, in schematic view, an electrophysiological heart catheter that includes catheter shaft 45, distal portion 44 and inflation port 47. Metering device 46 couples to inflation port 47 for injecting a controlled amount of fluid into balloon 48 through an inflation lumen extending the length of catheter shaft 45. Metering device 46 is preferably a screw syringe as used in balloon angioplasty.

As seen in FIG. 7, the balloon in uninflated condition has a diameter substantially corresponding to that of the catheter. Balloon 48 is made from elastomeric material which has a plurality of tightly spaced conductive dots 50 disposed on its surface. Tip electrode 49 is provided for sensing cardiac signals. Any number of ring electrodes may also be disposed along distal portion 44 to provide additional sensing capability.

FIG. 8 shows the balloon 48 inflated to a mid-size while FIG. 9 illustrates the balloon inflated more fully. The spacing between the dots allows the balloon to expand to a desired size. The size of the balloon can be precisely controlled by employing metering device 46. Electrode 52 is coupled to a suitable RF control unit via wire 53. Monopolar RF energy delivered to electrode 52 capacitively couples to conductive dots 50 which are used to ablate cardiac tissue. In this case, electrically conductive fluid is employed as the inflation medium for the balloon. Capacitive coupling occurs across the thickness of the balloon to the conductive dots on the surface of the balloon.

Figure 10:
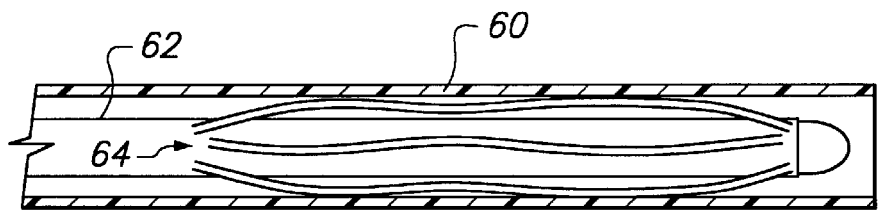
FIG. 10 is a side view of a distal portion of an electrophysiological heart catheter having a sheath that compresses a set of flexible members.
Figure 11:
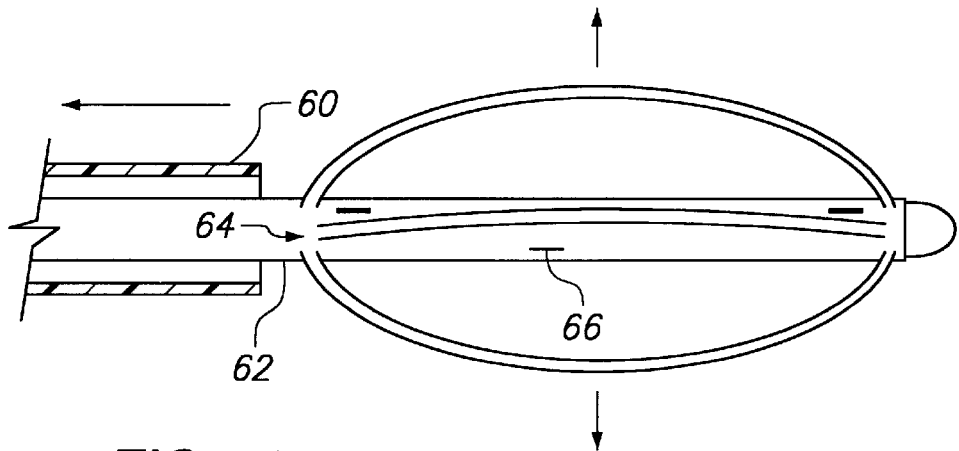
FIG. 11 is a side view of the electrophysiological heart catheter of FIG. 10, with the sheath retracted and the flexible members in an expanded condition.

The embodiments of FIGS. 10 and 11 employ a retractable sheath 60 to compress flexible members 64 to conform substantially to the diameter of catheter shaft 62 for navigation through the venous system and into the heart. Flexible members 64 are either made from conductive material or are coated with a conductive material for suitably receiving RF energy to ablate cardiac tissue. The conductive material is preferably gold.

FIG. 10 shows the sheath extended to the distal end of catheter shaft 62 thereby restraining flexible members 64. FIG. 11 shows sheath 60 retracted proximally of the catheter, allowing the flexible members to expand away from catheter shaft 62.

Sensing electrodes 66 are longitudinally disposed along the length of the catheter shaft. FIGS. 10 and 11 show sensing electrodes 66 axially rotated relative to each other. Each electrode shown has a corresponding electrode mounted on the opposite side of the catheter shaft in the plane perpendicular to the longitudinal axis of the catheter shaft. These electrodes form orthogonal electrode pairs for sensing local cardiac electrical signals. Alternatively, sensing ring electrodes could be disposed along catheter shaft 62. A sensing and/or ablation tip electrode may also be disposed at the distal tip of the catheter shaft.

In an alternative embodiment the catheter shaft could comprise two slidably moveable segments having an extended position and a retracted position. The extended position is characterized by having a tensioning wire maintaining the distal ends of the moveable segments farthest apart, while the retracted position is characterized by releasing the tension in the tensioning wire and having the distal ends of the moveable segments move closer together. Flexible members 64 are mounted such that the two ends of each member are connected to different segments of the catheter shaft. With the catheter segments in the extended position the flexible members are drawn against the catheter shaft, while in the retracted position the flexible members bow away from the catheter shaft.

The embodiments of FIGS. 12 through 16 employ catheter shafts having two slidably moveable segments, the inner segment having an extended position and a retracted position as described above.

Figure 12:
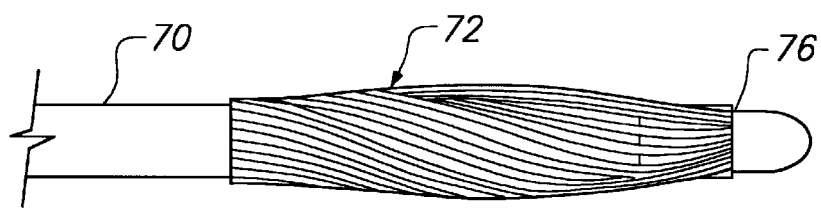
FIG. 12 is a side view of a distal portion of an electrophysiological heart catheter shaft having a set of flexible members drawn tightly around the catheter shaft.
Figure 13:
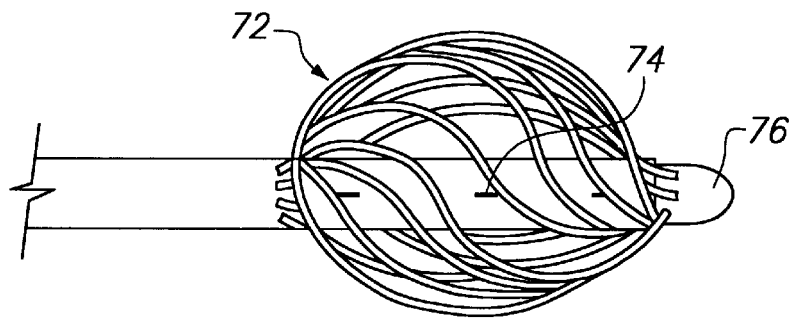
FIG. 13 is a side view of the electrophysiological heart catheter of FIG. 12, showing the flexible members expanded away from the catheter shaft.

FIG. 12 shows inner catheter segment 76 in the extended position, with flexible members 72 drawn against outer catheter segment 70. FIG. 13 shows inner catheter segment 76 in the retracted position, segment 76 resting deeper within segment 70 than in FIG. 12. As shown in FIG. 13, in the retracted position flexible members 72 bow away from the catheter shaft providing a larger ablation region. If a more spatially uniform ablation is desired, a greater number of flexible members may be employed.

Sensing electrodes 74 can be disposed along the catheter shaft for sensing. A sensing and/or ablation electrode can also be included at the distal tip of catheter segment 76.

Figure 14:
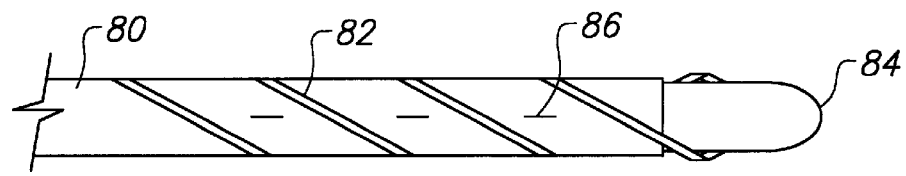
FIG. 14 is a side view of a distal portion of an electrophysiological heart catheter shaft having a set of flexible members wrapped tightly around the catheter shaft.
Figure 15:
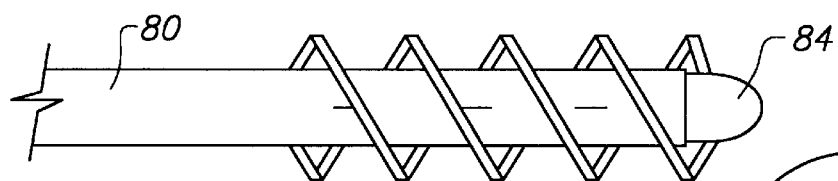
FIG. 15 is a side view of the electrophysiological heart catheter shaft of FIG. 14, showing the flexible members expanded away from the catheter shaft.

Another embodiment is shown in FIGS. 14 and 15. FIG. 14 illustrates the distal segment 84 in an extended position (distal segment 84 being pulled out from segment 80). In the extended position alternating flexible members 82 are drawn against the catheter shaft. FIG. 15 shows distal segment 84 in the retracted position (segment 84 being retracted inside segment 80), allowing flexible members 82 to extend away from the catheter shaft.

Figure 16:
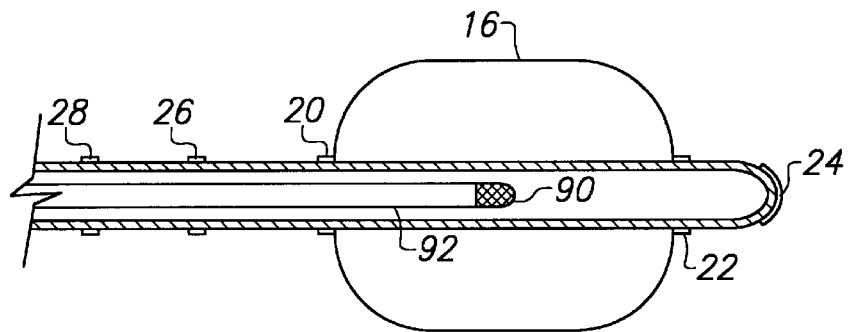
FIG. 16 is a partially sectional view of the distal portion of a catheter of the type shown in FIG. 3 that additionally includes an ultrasound transducer.

In certain circumstances it is advantageous to employ ultrasound imaging in connection with the ablation technique. FIG. 16 shows a sectional view of the catheter shown in FIG. 3, taken along the line I—I, the catheter additionally including an ultrasound transducer 90 coupled to drive shaft 92, which extends the entire length of the catheter through a lumen disposed therein. Ultrasound imaging can be used to monitor the lesion forming during ablation. It is contemplated that ultrasound imaging could be employed with any of the embodiments described. Details of ultrasound imaging catheters are described in a U.S. patent application entitled "Catheters for Imaging, Sensing Electrical Potentials, and Ablating Tissue," by Robert J. Crowley, filed the same day as the present application, the entire disclosure of which is hereby incorporated herein by reference.

Figure 27:
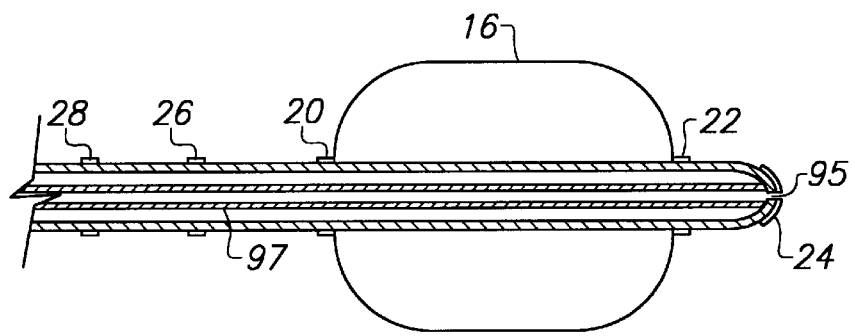
FIG. 27 is a partially sectional view of the distal portion of a catheter of the type shown in FIG. 3 that additionally includes a port for introduction of fluid to an ablation site.

In other instances, it is advantageous to provide a fluid dispensing lumen as part of the catheter for the purpose of augmenting the ablation effect at the tissue. FIG. 27 shows a sectional view of the catheter shown in FIG. 3 taken along the line I—I, the catheter additionally including a dispensing lumen 97, which is coupled with a fluid dispenser at the proximal end of the catheter and feeds into dispensing port 95. The fluid introduced into the dispensing port may be selected to be highly electrically conductive relative to that of blood and thus can render the zone where the fluid is introduced to tissue at dispensing port 95 preferentially conductive and thus create a zone where most of the ablative current will flow. Other fluids, such as alcohol, may be added to augment the ablation effect. The dispensing port may be located at any desirable location on the distal portion of the catheter.

FIGS. 17 through 21, which show a catheter extending through the left atrium of a heart and into the left ventricle, illustrate a typical method of use for the balloon electrode embodiments of FIGS. 1 through 9. The left side of the heart is typically accessed by inserting the distal end of a catheter in an opening in the femoral vein of a patient and navigating the catheter through the venous system. Other chambers of the heart are also accessible to the invention and are treatable by means of catheters according to the invention.

Figure 18:
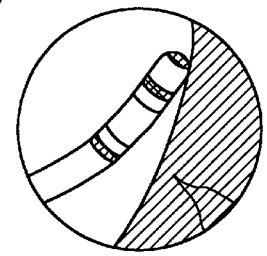
FIG. 18 is an enlarged view of a portion of FIG. 17.
Figure 17:
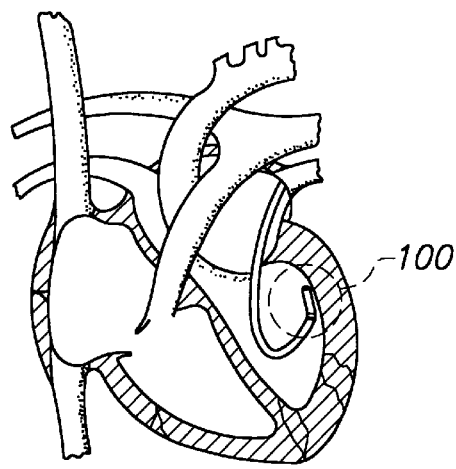
FIG. 17 is a partially cross-sectional view of a catheter in the left side of a heart, showing a balloon electrode in a deflated condition and in contact with heart tissue.

FIG. 17 shows the deflected distal end of a catheter shaft extending through the left atrium of a heart and positioned against a wall of the ventricle. FIG. 18 shows an enlarged view of the portion of FIG. 17 contained in region 100. Positioned against the heart wall, the ring electrodes and the distal tip electrode can be employed to locate regions of cardiac tissue to be ablated.

Figure 19:
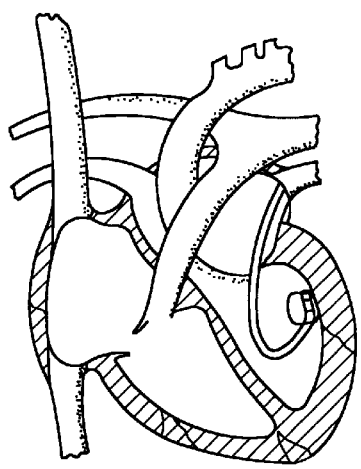
FIG. 19 is a partially cross-sectional view of a catheter in the left side of a heart, showing a balloon electrode in an inflated condition.
Figure 20:
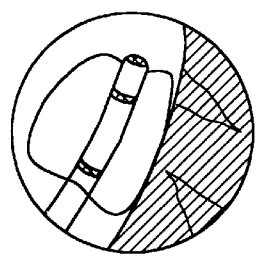
FIG. 20 is an enlarged view of a portion of FIG. 19.

Once an ablation site has been located, the balloon electrode is controllably inflated to the desired size, corresponding to the area of the ablation region, and is pressed against the tissue at the ablation site as shown in FIGS. 19 and 20. The tissue is ablated in accordance with the electrode embodiment employed. The ablation effect may be augmented by introducing conductive fluid or alcohol to the ablation site. During the ablation, ultrasound imaging can be employed to observe the resulting lesion being formed. Alternatively, the ring or distal tip electrodes may be used to sense electrical potentials during the ablation procedure.

Figure 21:
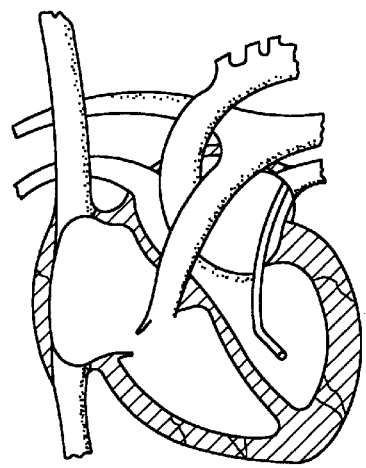
FIG. 21 is a partially cross-sectional view of a catheter in the left side of a heart, showing a balloon electrode in a deflated condition and removed from contact with heart tissue.

FIG. 21 shows the catheter with a deflated balloon electrode approaching a different wall of the ventricle, where the above procedure can be repeated if necessary.

FIGS. 22 through 26 illustrate a typical method of use for the mechanical electrode embodiments of FIGS. 10 through 15. Specifically, the embodiment of FIGS. 10 and 11 is illustrated, although the other embodiments would function similarly.

FIG. 22 shows the deflected distal end of a catheter shaft extending through the left atrium of a heart and positioned against a wall of the ventricle. FIG. 23 shows an enlarged view of the portion of FIG. 22 contained in region 130. Positioned against the heart wall, the mapping electrodes can be employed to locate regions of cardiac tissue to be ablated.

Once an ablation site has been located, the mechanical electrode is controllably expanded to the desired size, corresponding to the area of the ablation region, and is pressed against the tissue at the ablation site as shown in FIGS. 24 and 25. The tissue is ablated by passing RF current between the mechanical electrode and an electrode external to the patient's body in a monopolar configuration. The ablation effect may be augmented by introducing conductive fluid or alcohol to the ablation site. During the ablation, ultrasound imaging can be employed to observe the resulting lesion being formed. Alternatively, the mapping electrodes may be used to sense electrical potentials during the ablation procedure.

FIG. 26 shows the catheter with a retracted mechanical electrode approaching a different wall of the ventricle, where the above procedure can be repeated if necessary.

Other embodiments are within the following claims. For example, the expandable balloons in accordance with the present invention may be heated balloons of the type described in a U.S. patent application entitled "Ablation Catheters," by Charles D. Lennox et al., filed on the same day as the present invention, the entire disclosure of which is hereby incorporated by reference herein.

What is claimed is:

1. A catheter device, comprising:
    an elongated, flexible catheter shaft comprising an expandable portion;
    an ablation electrode located on said expandable portion of the catheter shaft and constructed to access a heart; and
    an electrical conductor located on said catheter shaft and positioned to capacitively couple radio-frequency energy to said electrode to cause said electrode to produce a burn lesion;
    said catheter shaft portion being expansible in diameter from a small profile to a large profile;
    said catheter shaft portion being sufficiently small and flexible in said small profile to maneuver into said heart through a tortuous path, and being more rigid in said large profile to permit a conductive surface of said electrode to be pressed against heart tissue with suitable contact pressure.

2. A catheter device in accordance with claim 1, wherein said electrode is substantially thermally conductive.

3. A catheter device in accordance with claim 1, wherein the electrode is a monopole electrode.

4. A catheter device in accordance with claim 1, wherein said expandable shaft portion comprises a balloon.

5. A catheter device in accordance with claim 4, wherein an exterior portion of said balloon is coated with a coating of an electrically and thermally conductive material.

6. A catheter device in accordance with claim 5, wherein said coating is of a pattern chosen to enable said balloon to stretch.

7. A catheter device in accordance with claim 6, wherein said pattern is a series of metal conductive dots applied to an exterior surface of said balloon.

8. A catheter device in accordance with claim 7, wherein said balloon is constructed to enable capacitive coupling between said dots and an electrically conductive fluid employed as an inflation medium for said balloon.

9. A catheter device in accordance with claim 8, further comprising an electrode mounted on said catheter shaft and extending into said balloon, said electrode being configured to provide electrical current to fluid within said balloon when said balloon is inflated.

10. A catheter device in accordance with claim 4, wherein said balloon is constructed of a compliant material and is constructed to permit a user to select an outer dimension of said balloon when inflated by selecting a volume of inflation fluid that is introduced into said balloon to inflate said balloon.

11. A catheter device in accordance with claim 10, wherein said compliant material is an elastomer.

12. A catheter device in accordance with claim 4, further comprising a high-accuracy screw syringe attached to said catheter shaft and constructed to precisely control the amount of fluid introduced to said balloon.

13. A catheter device in accordance with claim 4, further comprising an additional electrode disposed on said catheter shaft.

14. A catheter device in accordance with claim 13, wherein said additional electrode is an electrophysiological mapping electrode.

15. A catheter device in accordance with claim 1, further comprising an ultrasound imaging device incorporated into said catheter shaft.

16. A catheter device in accordance with claim 1, further comprising a fluid dispensing lumen in said catheter shaft.

17. A catheter device, comprising:
    an elongated, flexible catheter shaft;
    an first electrode disposed on said catheter shaft; and
    a second electrode disposed within the shaft and separated from the first electrode by a dielectric, such second electrode being positioned with respect to the first electrode to capacitively couple radio frequency energy to the second electrode through the dielectric.

18. The catheter device recited in claim 17 wherein the shaft has an expandable portion and wherein the first electrode is disposed on the expandable portion of the shaft.

19. The catheter recited in claim 18 wherein the expandable portion of the shaft comprises a balloon.

20. The catheter recited in claim 17 wherein the shaft has disposed thereon a plurality of first electrodes, each one thereof being capacitively coupled to said second electrode.

21. The catheter device recited in claim 20 wherein the shaft has an expandable portion and wherein the plurality of first electrodes are disposed on the expandable portion of the shaft.

22. A method of coupling energy to an electrode disposed on an elongated, flexible catheter shaft, comprising;

disposing a radio frequency energy coupling electrode within the shaft and separated from the first mentioned electrode by a dielectric, such coupling electrode being positioned with respect to the first mentioned electrode to capacitively couple radio frequency energy to the first mentioned electrode through the dielectric; and capacitively coupling radio frequency energy from the coupling electrode to the first mentioned electrode through the dielectric.

\* \* \* \* \*